United States Patent [19]

Nakagawa et al.

[11] Patent Number: 5,281,277
[45] Date of Patent: Jan. 25, 1994

[54] LIQUID COMPOSITION FOR CONTACT LENSES AND METHOD FOR CLEANING A CONTACT LENS

[75] Inventors: Akira Nakagawa; Satoko Kondo; Yoshiko Oi, all of Nagoya, Japan

[73] Assignee: Tomei Sangyo Kabushiki Kaisha, Nagoya, Japan

[21] Appl. No.: 865,268

[22] Filed: Apr. 8, 1992

[30] Foreign Application Priority Data

Apr. 8, 1991 [JP] Japan .................. 3-103096
Feb. 5, 1992 [JP] Japan .................. 4-56388

[51] Int. Cl.$^5$ .......................... A61L 2/04; C11D 7/42; C11D 7/50; C12N 9/96
[52] U.S. Cl. ........................... 134/18; 134/30; 134/42; 252/135; 252/139; 252/153; 252/173; 252/174.12; 252/523; 252/DIG. 12; 252/DIG. 14; 422/26; 422/28; 435/188; 514/839
[58] Field of Search .............. 252/106, 174.12, 187.21, 252/186.33, DIG. 12, 135, 139, 173, 153, 523, DIG. 14; 134/18, 30, 42; 422/26, 38; 435/188; 514/839

[56] References Cited

U.S. PATENT DOCUMENTS

| | | |
|---|---|---|
| 3,910,296 | 10/1975 | Karageozian et al. ......... 252/174.12 |
| 4,404,115 | 9/1983 | Tai ........................ 252/135 |
| 4,462,922 | 7/1984 | Boskamp .................. 252/174.12 |
| 4,537,706 | 8/1985 | Severson .................. 252/545 |
| 4,614,549 | 9/1986 | Ogunbiyi et al. ........... 252/174.12 |
| 4,670,179 | 6/1987 | Inamorato ................. 252/174 |
| 4,690,773 | 9/1987 | Ogunbiyi et al. ........... 252/174.12 |
| 4,900,366 | 2/1990 | Sibley et al. ............. 252/DIG. 14 |
| 4,959,179 | 9/1990 | Aronson ................... 252/135 |

FOREIGN PATENT DOCUMENTS

| | | | |
|---|---|---|---|
| 0080748 | 6/1983 | European Pat. Off. . | |
| 0141607 | 5/1985 | European Pat. Off. . | |
| 0348183 | 12/1989 | European Pat. Off. | 252/174.12 |
| 0462460 | 12/1991 | European Pat. Off. . | |
| 2369338 | 5/1978 | France . | |
| 2079305 | 1/1982 | United Kingdom | 252/174.12 |

*Primary Examiner*—Dennis Albrecht
*Attorney, Agent, or Firm*—Oblon, Spivak, McClelland, Maier & Neustadt

[57] ABSTRACT

A liquid composition for contact lenses, having from 5 to 40% (w/v) of glycerol and from 4 to 20% (w/v) of boric acid and/or a borate incorporated to a solution containing an effective amount of a protease, in such a ratio that the boric acid and/or the borate is from 10 to 100 parts, preferably 10-20 parts, by weight per 100 parts by weight of the glycerol.

7 Claims, No Drawings

LIQUID COMPOSITION FOR CONTACT LENSES AND METHOD FOR CLEANING A CONTACT LENS

The present invention relates to a liquid composition for contact lenses and a method for cleaning a contact lens. More particularly, it relates to a cleaning solution for contact lenses, which is useful for both water non-containing contact lenses and water containing contact lenses, and a method for cleaning a contact lens by means of such a cleaning solution.

Contact lenses are generally classified into those made of water containing material and those made of water non-containing material. As water containing contact lenses, those made essentially of polyhydroxyethyl methacrylate or polyvinyl pyrrolidone, are known. As water non-containing contact lenses, those made essentially of polymethyl methacrylate or silicone rubber, and those made of an oxygen-permeable copolymer of polysiloxanyl methacrylate with methyl methacrylate, are known. With contact lenses made of water containing material among them, components in a cleaning solution or in a preserving solution, are likely to penetrate into the lenses. Therefore, if such a treating solution contains an irritant component or if the osmotic pressure of such a treating solution is excessively high beyond the physiological level, irritation or conjunctival hyperemia is likely to be brought about when the lenses are put on the eyes. Accordingly, it is necessary to pay a due attention to the safety and the concentrations of components constituting the treating solution.

When contact lenses are put on the eyes, soils such as proteins derived from lacrimal components tend to deposit thereon, whether the contact lenses are water containing or water non-containing. It has been common to employ a method to decompose and remove them by means of a protease. Such a protease is unstable in a solution state, and it gradually loses its activity. Therefore, it is difficult to supply such a protease in a solution state to the user. Therefore, it has been common to supply it in the form of a solid formulation such as a tablet, a granule or a powder, so that the user may use it by dissolving the formulation in e.g. purified water, as the case requires. However, in this method, the protease in a solid state has to be dissolved each time of its use, thus presenting cumbersomeness to the user.

On the other hand, in the application fields of cleaning agents, foods, etc., a method has been proposed to maintain the protease activity in a solution for a long period of time by an addition of a stabilizer (Japanese Examined Patent Publications No. 152/1966 and No. 131386/1981). However, ethanol or the like used as the stabilizer in such a method, is known to present an adverse effect to lens material and therefore can not be used for contact lenses.

Japanese Examined Patent Publication No. 28515/1978 proposes a method for stabilizing an enzyme by adding at least 5% of sorbitol and at least about 20% of the weight of this sorbitol, of borax. However, by the combination of sorbitol and borax, no adequate enzyme stability can be attained, and the compatibility with a surfactant is poor, whereby if a surfactant is added at a high concentration, separation is likely to occur.

On the other hand, as a treating solution for contact lenses, Japanese Unexamined Patent Publication No. 167726/1989 discloses a preserving solution having an enzyme incorporated together with a water-soluble polymer containing quaternary ammonium groups and hydroxyl groups. However, this preserving solution had low cleaning effects and was not adequate as a cleaning solution. Further, Japanese Unexamined Patent Publications No. 159822/1988 and No. 180515/1989 propose a method for stabilizing a protease by incorporating a protease to a solution containing at least 50% of an organic liquid miscible with water. However, the enzymatic activity obtainable with this solution was very low, and cleaning effects were practically inadequate. In addition, the osmotic pressure of the solution tended to be very high, and it was practically impossible to use such a method for water containing contact lenses.

Further, among conventional stabilized enzyme solutions for contact lenses, there are some which are to be diluted at the time of use in order to obtain high enzymatic activities. However, such stabilized enzyme solutions usually contain a large amount of a stabilizing component such as glycerol. Therefore, when they are diluted with e.g. a commercially available preserving solution, the osmotic pressures of such solutions tend to be so high that they can not be used for cleaning water containing contact lenses. Therefore, they have been useful only for water non-containing contact lenses. It would be possible to bring the osmotic pressure of a diluted solution close to the physiological level by diluting at a high diluting rate with purified water having no substantial osmotic pressure or very low osmotic pressure or with purified water containing an anticeptic. However, in such a case, the user has to purchase a diluting solution of exclusive use separately.

The present invention has been accomplished under these circumstances. It is an object of the present invention to stabilize the enzyme in a solution while suppressing the osmotic pressure of the solution at a relatively low level and thereby to provide a cleaning solution for contact lenses having high cleaning effects, which can safely and readily be used not only for water non-containing contact lenses but also for water containing contact lenses. It is another object of the present invention to provide a method for effectively cleaning a contact lens by means of such a liquid composition.

As a result of an extensive research, the present inventors have found it possible to maintain a protease activity in a solution under a stabilized condition while preventing the osmotic pressure from departing excessively from the physiological level by using glycerol, and boric acid and/or a borate in combination as the enzyme-stabilizing component.

Thus, the present invention has been accomplished on the basis of such a discovery and provides a liquid composition for contact lenses, having from 5 to 40% (w/v) of glycerol and from 4 to 20% (w/v) of boric acid and/or a borate incorporated to a solution containing an effective amount of a protease, in such a ratio that the boric acid and/or the borate is from 10 to 100 parts by weight per 100 parts by weight of the glycerol. Further, such a liquid composition of the present invention preferably contains, in addition to the above components, a surfactant in an amount of not higher than 30% (w/v).

The present invention also provides a method for cleaning a contact lens, which comprises diluting the above liquid composition for contact lenses, with an aqueous medium, and contacting the contact lens to the diluted solution thereby obtained, to remove a soil deposited on the contact lens. In the cleaning method of the present invention, it is preferred that the contact lens is contacted to the diluted solution at a temperature of from 5° to 80° C. for from one minute to 24 hours, followed by boiling for sterilization in the diluted solution.

Now, the present invention will be described in detail with reference to the preferred embodiments.

In summary, the liquid composition for contact lenses according to the present invention is the one whereby a protease is stabilized in a solution having a low osmotic pressure by a synergistic effect of glycerol, and boric acid and/or a borate, and it has a feature that it is safely useful not only for contact lenses made of water non-containing material but also for contact lenses made of water containing material.

Among the components constituting the liquid composition for contact lenses of the present invention, glycerol is mild in its activity against a vital body and has been frequently used as a stabilizer for an enzyme. In the present invention, it is incorporated in an amount of from 5 to 40% (w/v). If the concentration of glycerol in the liquid composition is lower than 5% (w/v), no adequate enzyme stability can be attained. On the other hand, if it is higher than 40% (w/v), the osmotic pressure tends to be too high, whereby if rinsing is inadequate at the time of cleaning a water containing contact lens, irritation to the eye is likely to be brought about.

On the other hand, boric acid or a borate has a certain stabilizing power and is mild in its action against a vital body and free from irritating activity. Therefore, it is widely used for cleaning eyes or cleaning or disinfecting the conjunctival sacs, and it is highly safe to eyes. In the present invention, such boric acid and a borate are incorporated in a total amount of from 4 to 20% (w/v). If the concentration of the boric acid and/or the borate in the liquid composition is lower than 4% (w/v), no adequate enzyme stability can be attained, and if it is higher than 20% (w/v), no further improvement in the enzyme stabilizing effects can be observed, and the osmotic pressure tends to be too high, whereby if rinsing is inadequate at the time of cleaning a water containing contact lens, irritation to eyes is likely to be brought about. Boric acid and/or a borate has been often used as a component of a buffer solution for an enzyme, but in such a case, it is used at a concentration at a level of not higher than 1% (w/v). In the present invention, either one of boric acid and a borate may be employed, or they may be used as a mixture. Which one should be used, or in what proportions they should be mixed, is determined depending upon the pH value to which the liquid composition for contact lenses of the present invention should be adjusted. The pH of the liquid composition is determined within a pH range wherein there will be no irritation to eyes and the protease is stable. Specific examples of the borate include borax, potassium borate, lithium borate, ammonium borate and triethanolamine borate.

None of the mechanism for stabilizing the enzyme by glycerol, the mechanism for stabilizing the enzyme by boric acid and/or a borate, and the mechanism for synergistically stabilizing the enzyme by such glycerol, and boric acid and/or a borate, is clearly understood. However, it is possible that glycerol deprives free water on the molecular surface of the enzyme protein and forms a composite with the enzyme by a hydrogen bond to stabilize the three dimensional structure of the enzyme. Further, boric acid and/or a borate is known to react with a polyhydric alcohol having many hydroxyl groups to form a complex compound. Here, it is possible that it reacts with hydroxyl groups of e.g. serine, threonine or tyrosine abundantly present on the molecular surface of the enzyme protein, to stabilize the three dimensional structure of the enzyme. Further, as a reason for further improvement of the enzyme-stabilizing effects by mixing glycerol with boric acid and/or a borate, it is conceivable that the boric acid and/or the borate is linked with hydroxyl groups of both the enzyme and the glycerol, so that it plays a role of a bridge connecting them. However, the functional mechanisms are not clearly understood.

As described above, glycerol, and boric acid and/or a borate will form a complex compound, whereby the numbers of molecules will not be accumulative. Accordingly, by mixing glycerol with boric acid and/or a borate, the osmotic pressure of the liquid composition for contact lenses will be lower than the sum of osmotic pressures of the constituting components. Thus, it is possible to advantageously stabilize the enzyme under an osmotic pressure lower than that under which it is stabilized by the respective components.

As described in Commentary on Japanese Pharmacopoeia (11th Edition), the solubility of boric acid and/or a borate is much better in glycerol than in water. Namely, in water, only about 5% (w/v) of boric acid and/or a borate can be dissolved, while in glycerol, as much as about 50% (w/v) of boric acid and/or a borate can be dissolved. Accordingly, if boric acid and/or a borate is incorporated together with glycerol as in the case of the liquid composition for contact lenses of the present invention, it is possible to dissolve a large amount of boric acid and/or a borate, whereby it is possible to effectively increase the stability of a protease.

In the present invention, boric acid and/or a borate is incorporated in an amount of from 10 to 100 parts by weight per 100 parts by weight of glycerol in order to obtain an adequate enzyme-stabilizing effect. Namely, if the amount of boric acid and/or a borate is less than 10 parts by weight per 100 parts by weight of glycerol, the enzyme stability at a high temperature remarkably deteriorates. A long term stability at a high temperature is not required for the liquid composition for contact lenses. However, in a closed room in summer time, the temperature is likely to be temporarily as high as 60° C. or more. Therefore, it is desired that excellent stability can be maintained even under such a severe condition. On the other hand, if the amount of boric acid and/or a borate exceeds 100 parts by weight per 100 parts by weight of glycerol, not only a long term enzyme stability at a moderate temperature of about 40° C., tends to deteriorate, but also the solubility of the liquid composition tends to be close to be saturation, whereby it tends to be difficult to dissolve other components such as a surfactant. Preferably, boric acid and/or a borate is incorporated in an amount of from 10 to 20 parts by weight per 100 parts by weight of glycerol.

Proteases are generally classified into four types of serine proteases, thiol proteases, metal proteases and carboxyl proteases, depending upon the respective active sites. Among them, thiol proteases have thiol groups as the active catalytic sites, whereby a reducing agent such as cysteine or thiourea is required. However, such a reducing agent has a problem that it is readily oxidized by oxygen in air, and it is difficult to maintain it under a stabilized condition in a liquid formulation. A metal protease has a metal such as zinc as the active catalytic site. A commercially available preserving solution for contact lenses used as an aqueous medium in the cleaning method of the present invention, often contains a metal chelating agent, and the metal protease is likely to be inactivated by such a metal chelating agent. Further, a carboxyl protease is a protease commonly called an acidic protease, which has an enzymatic activity in an acidic region. However, it is undesirable that a liquid formulation which is to be in contact with a finger or an eye as the liquid composition for contact lenses, has its pH within a strongly irritating acidic region.

Whereas, the serine protease is a protease having serine residues at its active catalytic sites, and it is known that such a serine protease is deactivated by a reagent such as diisopropylfluoro phosphoric acid or phenylmethanesulfonyl fluoride which specifically bonds to serine residues. Depending upon the inactivation mode against such a reagent, a substance is determined as to whether or not it is a serine protease. This enzyme requires no reducing agent, is not influenced by a metal chelating agent and has an optimum pH for enzymatic activity around a neutral region. Thus, it is suitable for use in the present invention.

Specific examples of the serine protease include trypsin and chymotripsin derived from animals, Streptomyces protease derived from actinomycetes, Bacillus protease derived from bacteria and Aspergillus protease derived from mold. Further, various types of such protease are commercially available, including, for example, "Bioprase" (manufactured by Nagase Seikagaku Kogyo K.K.), "Alcarase", "Esperase", "Sabinase", "Subtilisin A", "PEM" (manufactured by Novo Nordisk Bioindustry Ltd.), "Protease N AMANO" "Protease P AMANO" (manufactured by Amano Pharmaceutical Co., Ltd.) and "Actinase AS" (manufactured by Kaken Pharmaceutical Co., Ltd.). For practical use, a suitable protease will be selected among them. Among the commercial products, there are some in which a protease other than the serine protease, or a carbohydrolytic enzyme or a lipolytic enzyme such as amylase or lipase, may inevitably be included during the process for their purification.

In the present invention, the amount of the protease to be incorporated, is determined suitably dependent upon the effective amount corresponding to the desired cleaning effects, and it is usually preferably from 0.01 to 20% (w/v), more preferably from 0.1 to 10% (w/v). If the amount is too small, the cleaning effects tend to be inadequate. On the other hand, if the enzyme concentration is too high, there will be a possible danger of damaging the skin during the cleaning operation.

Among proteases, there are some which have, in their molecules, sites linkable with calcium ions and which take more stabilized molecular structures as they take calcium ions in their molecules. When such proteases are used, it is advisable to further improve their stability by adding calcium ions in an amount of from 0.01 to 0.2% (w/v). As a source for supplying such calcium ions, calcium chloride, calcium nitrate or calcium acetate is, for example, preferred which has excellent solubility in water.

To the liquid composition for contact lenses of the present invention, it is advantageous to add a prescribed surfactant at a concentration of not higher than 30% (w/v) to remove lipid soil such as lema deposited on contact lenses. In such a case, any one of nonionic surfactants, anionic surfactants and amphoteric surfactants may be employed.

For example, specific examples of nonionic surfactants include a polyoxyehtylene polyoxypropylenealkyl ether, a sorbitan fatty acid ester, a glycerol fatty acid ester, a polyglycerol fatty acid ester, a polyoxyethylenesorbitan fatty acid ester, a polyoxyehtylenesorbit fatty acid ester, a polyoxyehtyleneglycerol fatty acid ester, a polyethyleneglycol fatty acid ester, a polyoxyethylenealkyl ether, a polyoxyethylenealkylphenyl ether, a polyoxyethylene hardened castor oil, a polyoxyethylenealkylamine and a polyoxyethylene fatty acid amide.

Specific examples of the anionic surfactants include an alkyl sulfate, a polyoxyethylenealkyl ether sulfate, an N-acyl-amino acid salt, a polyoxyethylenealkyl ether acetate, an alkyl sulfocarboxylate, an α-olefin sulfonate and a polyoxyethylenealkyl ether phosphate.

The amphoteric surfactants include, for example, an alkyldimethylaminoacetic acid betaine, a fatty acid amide propyldimethylaminoacetic acid betaine and a 2-alkyl-N-carboxymethyl-N-hydroxyethylimidazolinium betaine.

Among such various surfactants, one or more may suitably be selected for incorporation. For the preparation of the liquid composition for water containing contact lenses, it is advisable to select the one having no or low irritating effects to the eyes.

Further, to the liquid composition for contact lenses of the present invention, various additives such as pH-controlling agents and preservatives, which are commonly employed, may be incorporated, as the case requires, in addition to the above-mentioned components. For example, the liquid composition for contact lenses is usually preferably adjusted to a pH of from 5 to 10, preferably from 6 to 9 to reduce irritation to the eyes or to stabilize the protease. Accordingly, a pH-controlling agent such as hydrochloric acid, acetic acid, sodium hydroxide, potassium hydroxide, triethanolamine or tris(hydroxymethyl)aminomethane, is added in a suitable amount, as the case requires. Further, an preservative is usually incorporated in an amount within a range of from 0.001 to 1% (w/v). As such a preservative, potassium sorbate, sodium sorbate, sodium benzoate, a p-oxybenzoic acid methyl ester, ethyl ester or propyl ester, a polyhexamethylenebiguanide hydroxide, alexygine dihydrochloride, chlorohexygine gluconate, benzalconium chloride, α-4-[1-tris(2-hydroxyethyl)ammonium chloride-2-butenyl]poly[1-dimethylammonium chloride-2-butenyl]-ω-tris(2-hydroxyethyl)ammonium chloride, an $N^a$-cocoil-L-alginine ethyl ester.DL-pyrrolidone carboxylate, (wherein a=α) or glyceryl monolaurate may, for example, be used.

The liquid composition for contact lenses of the present invention thus prepared by mixing the above-mentioned various components, will be diluted with a suitable aqueous medium when it is used for cleaning contact lenses. As the aqueous medium to be used here, any commercially available preserving solution or cleaning-preserving solution may be employed for cleaning treatment of water non-containing contact lenses, and a commercially available preserving solution having an osmotic pressure of not higher than about 400 mmol/kg, a physiological saline solution, purified water or a diluting solution of exclusive use containing an anticeptic, may be employed for cleaning treatment of water containing contact lenses.

The diluting ratio is usually preferably such that the liquid composition for contact lenses is in an amount of from 0.05 to 5 parts by volume per 100 parts by volume of the aqueous medium. If the amount of the liquid composition for contact lenses is lower than this range, the enzymatic activity tends to be inadequate, and the cleaning effects tend to be poor. On the other hand, if the amount exceeds the above range, the enzyme-stabilizing component in the liquid composition for contact lenses will be substantial in the diluting solution, whereby it is likely that the enzyme can not perform its effect adequately, or the osmotic pressure of the diluting solution tends to substantially depart from the physiological osmotic pressure, whereby when applied to water containing contact lenses, it tends to adversely affect the lens sizes, and if rinsing is inadequate, it presents irritation to the eyes when such contact lenses are put on the eyes.

As described above, the liquid composition for contact lenses of the present invention accomplishes stabilization of the enzyme at a relatively low osmotic pressure in the state prior to dilution. Therefore, even when diluted with a commercially available preserving solution adjusted to a physiological osmotic pressure or with a physiological saline solution, it is possible to avoid a substantial departure of the osmotic pressure after dilution from the physiological level. Thus, it has now been made possible to conduct cleaning treatment of contact lenses safely and simply even in the case of water containing contact lenses. The enzymatic activity can adequately be provided by dilution at the time of use, whereby excellent cleaning effects can be obtained.

When a contact lens is treated with the diluted solution of the liquid composition of the present invention, such treatment is conducted by leaving the contact lens for from one minute to 24 hours at a temperature of from 5° to 40° C. in the case of a water non-containing lens and at a temperature of from 5° to 80° C. in the case of a water containing contact lens. After such treatment, the water non-containing contact lens may be rinsed with running water and then used again. The water containing contact lens is subjected to usual sterilization by boiling in a diluting solution or in a commercially available preserving solution and then put on the eye. The higher the treating temperature, the higher the cleaning effects. However, the enzyme is usually unstable at a high temperature, and at a temperature of 80° C. or higher, the enzymatic activity drops rapidly, and no adequate effects will be obtained. Further, in the case of a water non-containing contact lens, it is known that an adverse effect to the lens standards may sometimes be brought about at a temperature of 40° C. or higher.

Now, the present invention will be described in further detail with reference to some Examples. However, it should be understood that the present invention is by no means restricted by such specific Examples. Further, it should be understood that various changes, modifications or improvements may be made on the basis of the common knowledge of those skilled in the art without departing from the spirit of the present invention, in addition to the following Examples and the specific embodiments described above.

EXAMPLE 1

To 40 ml of purified water, 32 g of glycerol, 5 g of borax, 0.1 g of calcium chloride and 15 g of polyoxyethylene (20) monooleate were mixed and dissolved under heating. To this solution, 4 g of Subtilisin A (tradename, protease, manufactured by Novo Nordisk Bioindustry Ltd.) was added and dissolved under stirring. The pH of the sample solution (liquid composition for contact lenses) thus obtained was measured by means of a pH meter F-8E Model, manufactured by Kabushiki Kaisha Horiba Seisakusho, and the activities of the protease were measured immediately after the preparation and after the storage for three months at a temperature of 40° C., whereupon the enzymatic activity remaining rate (%) was calculated by the following formula (1). As a result, the pH was 6.15, and the enzymatic activity remaining rate was 98.7%.

$$\text{Enzymatic activity remaining rate (\%)} = [\text{Enzymatic activity after storage/Enzymatic activity immediately after the preparation}] \times 100 \quad (1)$$

The activity of the protease was measured as follows.

Namely, 1 ml of a diluted solution prepared by diluting the sample solution (the liquid composition for contact lenses) with purified water so that the absorption at 275 nm would be within a range of from 0.3 to 0.7, was added to 5 ml of a 0.6% casein solution (a 0.08M monohydrogenphosphate aqueous solution, pH7.0) heated to 37° C., and the mixture was maintained at 37° C. for 10 minutes. Then, 5 ml of a precipitating reagent (a solution mixture comprising 0.11M trichloroacetic acid, 0.22M sodium acetate and 0.33M acetic acid) was added thereto, and the mixture was maintained at 37° C. for further 30 minutes to precipitate a non-decomposed protein, followed by filtration. After the filtration, absorption A at 275 nm of the filtrate was obtained. Separately, 1 ml of the diluted solution, 5 ml of the precipitating reagent and 5 ml of the casein solution were preliminarily added in this order, and the mixture was maintained at 37° C. for 30 minutes, followed by filtration. After the filtration, absorption $A_0$ at 275 nm of the filtrate was obtained. From A and $A_0$, the enzymatic activity is determined in accordance with the following formula (2). Further, an enzymatic activity capable of forming a non-protein substance showing an absorption at 275 nm in an amount corresponding to $1 \times 10^{-6}$ g of tyrosine per minute, was evaluated to be $1\mu$.

$$\text{Enzymatic activity } (\mu/\text{ml}) = [(A - A_0)/A_s] \times 50 \times (11/10) \times \text{Diluting times} \quad (2)$$

where $A_s = 0.391$ (absorption by 50 $\mu$g/ml of tyrosine at 275 nm), and the diluting times = (parts by volume of purified water + parts by volume of the sample solution)/parts by volume of the sample solution.

EXAMPLE 2

Sample solutions No. 1 to No. 4 were prepared in the same manner as in Example 1 to have compositions as identified in Table 1 given hereinafter. To sample solutions No. 1 and No. 2, hydrochloric acid was added in suitable amounts to adjust them at pH6.85 and pH6.50, respectively. To sample solutions No. 3 and No. 4, sodium hydroxide was added in suitable amounts to adjust them at pH7.48 and pH7.00, respectively. With respect to each of sample solutions thus obtained, the enzymatic activity remaining rate after leaving it for 3 hours at a temperature of 70° C., was measured in the same manner as in Example 1, and the results are also shown in Table 1. It is evident that in each case, the enzyme stability was excellent.

TABLE 1

| Composition (%) (w/v) | Sample Solution No. | | | |
|---|---|---|---|---|
| | 1 | 2 | 3 | 4 |
| Glycerol | 5 | 10 | 20 | 35 |
| Borax | 5 | 10 | 10 | 10 |
| Experase 8.OL*[1] | 1 | — | — | — |
| Subtilisin A*[1] | — | 2 | — | — |
| Actinase AS*[2] | — | — | 1 | — |
| Protease P (Amano)*[3] | — | — | — | 2 |
| Pronon 204*[4] | 5 | — | — | — |
| Polyoxyethylene (20) sorbitanemonooleate*[5] | — | — | 5 | — |
| Calcium chloride | 0.1 | 0.1 | — | 0.1 |
| Potassium sorbate | 0.1 | — | — | — |
| pH | 6.85 | 6.50 | 7.48 | 7.00 |
| Enzymatic activity remaining rate (%) | 86 | 86 | 82 | 84 |

Notes
*[1] Protease derived from bacteria, manufactured by Novo Nordisk Bioindustry Ltd.
*[2] Protease derived from Actinomycetes, manufactured by Kaken Pharmaceutical Co., Ltd.
*[3] Protease derived from mold, manufactured by Amamo Pharmaceutical Co., Ltd.
*[4] Nonionic surfactant, manufactured by Nippon Oil and Fats Co., Ltd.
*[5] Nonionic surfactant, manufactured by Wako Junyaku K. K.

COMPARATIVE EXAMPLE 1

A sample solution containing 35% of glycerol, 1.5% of borax, 2% of Subtilisin A and 0.1% of calcium chloride, was prepared, and hydrochloric acid was added in a suitable amount to adjust it at pH6.50. The sample solution thus obtained, was left to stand for 3 hours at a temperature of 70° C. Then, the remaining enzymatic activity was measured in the same manner as in Example 1. As a result, the enzymatic activity remaining rate was less than 5%.

COMPARATIVE EXAMPLE 2

A sample solution containing 10% of sorbitol, 10% of borax, 2% of Subtilisin A and 0.1% of calcium chloride, was prepared, and hydrochloric acid was added in a suitable amount to adjust it at pH6.50. The sample solution thus obtained, was left to stand for 3 hours at a temperature of 70° C. Then, the remaining enzymatic activity was measured in the same manner as in Example 1. As a result, the enzymatic activity remaining rate was 7.2%.

EXAMPLE 3

A water containing contact lens (Menicon Soft MA, manufactured by Menicon Co., Ltd.) having soil afixed by the use for a few months, was put into a storage case filled with 2.5 ml of a commercially available preserving solution for water containing contact lenses (Menisoak, manufactured by Menicon Co., Ltd.) having an osmotic pressure of 290 mmol/kg. Then, two drops (about 0.05 g) of the sample solution No. 1 of Example 2 were added as the liquid composition for contact lenses, and a cover was put on the case, followed by stirring uniformly. Then, the osmotic pressure of this solution was measured and found to be 305 mmol/kg. The above lens was soaked in this solution for two hours at room temperature. Then, the lens was rinsed with the preserving solution and observed by a microscope, whereby the soil was found to have been completely removed. Thus, cleaning of the contact lens was carried out safely and simply.

COMPARATIVE EXAMPLE 3

The operation was conducted in the same manner as in Example 3 using a commercially available enzyme cleaning solution for water non-containing contact lenses (Proteoff, manufactured by Menicon Co., Ltd.) instead of the liquid composition for contact lenses used in Example 3, whereby the osmotic pressure of the solution after addition of two drops (about 0.05 g) of Proteoff was as high as 448 mmol/kg. Therefore, it could not be used for cleaning a water containing contact lens.

EXAMPLE 4

A water non-containing contact lens (Menicon EX, manufactured by Menicon Co., Ltd.) having soil afixed by the use for a few months, was put into a storage case filled with 2.5 ml of a commercially available cleaning-preserving solution for water non-containing contact lenses ($O_2$ care, manufactured by Menicon Co., Ltd.). Then, two drops (about 0.05 g) of the sample solution No. 1 of Example 2 were added as the liquid composition for contact lenses, and a cover was put on the case, followed by stirring uniformly. Then, the lens was soaked in this solution for two hours at room temperature. Then, the lens was taken out and rinsed with tap water, and then it was observed by a microscope, whereby the soil was found to have been completely removed.

EXAMPLE 5

A water containing contact lens (Menicon Soft MA, manufactured by Menicon Co., Ltd.) having soil afixed by the use for a few months, was put into a vial filled with 5 ml of a commercially available preserving solution for water containing contact lenses (Menisoak, manufactured by Menicon Co., Ltd.) having an osmotic pressure of 290 mmol/kg. Then, one drop (about 0.03 g) of the sample solution of Example 1 was added as the liquid composition for contact lenses, and a cover was put on the case, followed by stirring uniformly. Then, the osmotic pressure of this solution was measured and found to be 311 mmol/kg. Then, the above lens was soaked in this solution for two hours at room temperature, and the lens was rinsed with the preserving solution for water containing contact lenses and observed by a microscope, whereby the soil was found to have been completely removed.

EXAMPLE 6

In the same manner as in Example 1, 10% (w/v) of glycerol, 10% (w/v) of boric acid, 2% (w/v) of Subtilisin A and 0.1% (w/v) of calcium chloride, were dissolved in purified water, and sodium hydroxide was added in a suitable amount to adjust the pH to 6.50. Then, the solution was left to stand for 3 hours at a temperature of 70° C. in the same manner as in Example 2, whereupon the enzyme activity remaining rate was measured and found to be 84%.

EXAMPLE 7

A water containing contact lens (Menicon Soft MA, manufactured by Menicon Co., Ltd.) having soil afixed by the use for a few months, was put into a storage case filled with 1.2 ml of a commercially available preserving solution for water containing contact lenses (Menisoak, manufactured by Menicon Co., Ltd.). Then, one drop (about 0.03 g) of the sample solution No. 2 of Example 2, was added to the preserving solution in the storage case, as the liquid composition for contact lenses, and a cover was put on the case, followed by stirring uniformly. Then, cleaning of the water containing contact lens was conducted by maintaining the case in a hot bath of 60° C. for 30 minutes, followed by boiling for sterilization in a commercially available boil-sterilizer (a Menicon Riser Mini, manufactured by Menicon Co., Ltd.). After the sterilization, the lens was observed by a microscope, whereby the soil was found to have been completely removed.

As described in the foregoing, the liquid composition for contact lenses of the present invention is capable of effectively maintaining the enzymatic activity while suppressing the osmotic pressure at a relatively low level by the synergistic effects of glycerol, and boric acid and/or a borate. Therefore, during the cleaning operation of a contact lens, it is possible to effectively prevent the osmotic pressure of the diluted solution from departing from the physiological level even when the liquid composition is diluted with a commercially available preserving solution for the contact lenses. Therefore, not only a water non-containing contact lens but also a water containing contact lens can safely be cleaned by diluting the composition at the time of its use and by a simple operation of merely contacting the contact lens with the diluted composition. Since the liquid composition can be used by diluting it with a commercially available preserving solution for contact lenses at the time of the cleaning operation, it is unnecessary to have a separate diluting solution of exclusive use.

What is claimed is:

1. A stable aqueous liquid composition for cleaning contact lenses, comprising 5 to 40% (w/v) of glycerol and from 4 to 8% (w/v) of boric acid and/or a borate incorporated to a solution containing an effective cleaning amount of a protease, in such a ratio that the boric acid and/or the borate is from 10 to 20 parts by weight per 100 parts by weight of the glycerol.

2. The liquid composition for cleaning contact lenses according to claim 1, which further contains not higher than 30% (w/v) of a surfactant.

3. The liquid composition for cleaning contact lenses according to claim 1, wherein the borate is borax, potassium borate, lithium borate, ammonium borate or triethanolamine borate.

4. The liquid composition for cleaning contact lenses according to claim 1, wherein the protease is in an amount of from 0.01 to 20% (w/v).

5. A liquid composition according to claim 1, further comprising from 0.01 to 0.2% (w/v) of a calcium salt.

6. A method for cleaning a contact lens, which comprises diluting the liquid composition for cleaning contact lenses as defined in claim 1, with an aqueous medium, and contacting the contact lens to the diluted liquid composition, to remove a soil deposited on the contact lens.

7. A method for cleaning a contact lens, which comprises diluting the liquid composition for cleaning contact lenses as defined in claim 1, with an aqueous medium, contacting the contact lens to the diluted liquid composition at a temperature of from 5° to 80° C. for 1 minute to 24 hours, followed by boiling for sterilization in the diluted liquid composition.

* * * * *

UNITED STATES PATENT AND TRADEMARK OFFICE
CERTIFICATE OF CORRECTION

PATENT NO. : 5,281,277
DATED : January 25, 1994
INVENTOR(S) : Akira NAKAGAWA, et al.

It is certified that error appears in the above-indentified patent and that said Letters Patent is hereby corrected as shown below:

On the title page, Item [54] and column 1, line 2, the title should read as follows:

--STABILIZED LIQUID PROTEASE COMPOSITION FOR CONTACT LENSES AND METHOD FOR CLEANING A CONTACT LENS--

Signed and Sealed this

Thirty-first Day of May, 1994

Attest:

BRUCE LEHMAN

Attesting Officer

*Commissioner of Patents and Trademarks*